(12) United States Patent
Gavard Molliard et al.

(10) Patent No.: US 9,138,405 B2
(45) Date of Patent: Sep. 22, 2015

(54) USE OF A NATURAL POLYSACCHARIDE GEL FOR THE PREPARATION OF AN INJECTABLE FORMULATION FOR TREATMENT OF ARTICULAR DEGENERATION

(75) Inventors: Samuel Gavard Molliard, La Roche sur Foron (FR); Olivier Benoit, Epagny (FR)

(73) Assignee: APTISSEN SA, Plan-les-Ouates (CH)

( * ) Notice: Subject to any disclaimer, the term of this patent is extended or adjusted under 35 U.S.C. 154(b) by 659 days.

(21) Appl. No.: 12/667,627

(22) PCT Filed: Jul. 2, 2008

(86) PCT No.: PCT/FR2008/000948
§ 371 (c)(1),
(2), (4) Date: Mar. 30, 2010

(87) PCT Pub. No.: WO2009/024670
PCT Pub. Date: Feb. 26, 2009

(65) Prior Publication Data
US 2010/0184720 A1 Jul. 22, 2010

(30) Foreign Application Priority Data
Jul. 2, 2007 (FR) ...................................... 07 04772

(51) Int. Cl.
| | | |
|---|---|---|
| A01N 43/04 | (2006.01) |
| A61K 31/715 | (2006.01) |
| A61K 9/00 | (2006.01) |
| A61K 31/728 | (2006.01) |
| A61L 2/00 | (2006.01) |
| A61L 26/00 | (2006.01) |
| A61K 9/06 | (2006.01) |
| A61K 47/10 | (2006.01) |

(52) U.S. Cl.
CPC ............ A61K 9/0024 (2013.01); A61K 31/728 (2013.01); A61L 2/0023 (2013.01); A61L 26/008 (2013.01); A61L 26/0052 (2013.01); A61K 9/06 (2013.01); A61K 47/10 (2013.01); A61L 2400/06 (2013.01)

(58) Field of Classification Search
CPC . A61L 26/008; A61L 2400/06; A61L 2/0023; A61K 9/0024; A61K 31/728
USPC .......................................................... 514/54
See application file for complete search history.

(56) References Cited

U.S. PATENT DOCUMENTS

| | | | | |
|---|---|---|---|---|
| 5,079,236 | A | * | 1/1992 | Drizen et al. .................... 514/54 |
| 5,095,037 | A | | 3/1992 | Iwamitsu et al. |
| 5,972,909 | A | | 10/1999 | Di Napoli |
| 2003/0203030 | A1 | | 10/2003 | Ashton et al. |
| 2004/0185021 | A1 | * | 9/2004 | Hubbard .................... 424/70.13 |
| 2005/0208095 | A1 | * | 9/2005 | Hunter et al. ................. 424/423 |
| 2007/0196426 | A1 | | 8/2007 | Hermitte et al. |
| 2011/0230438 | A1 | * | 9/2011 | Bos ................................. 514/54 |

FOREIGN PATENT DOCUMENTS

| | | |
|---|---|---|
| EP | 0 297 860 | 1/1989 |
| EP | 0 499 164 | 8/1992 |
| FR | 2 865 737 | 8/2005 |
| WO | 2006/067608 | 6/2006 |
| WO | WO 2007/077399 A2 * | 7/2007 ............. A61Q 19/08 |

OTHER PUBLICATIONS

"Viscosity" from Cole-Parmer's FoodTechSource [online], [retrieved Jul. 14, 2009]. Retrieved from the internet <http://www.foodtechsource.com/rcenter/tech_data/td_viscosity.htm>.*
International Search Report dated Mar. 9, 2009, from corresponding PCT application.

* cited by examiner

Primary Examiner — Scarlett Goon
(74) Attorney, Agent, or Firm — Young & Thompson

(57) ABSTRACT

A sterile injectable aqueous formulation in the form of a gel is made up of hyaluronic acid (or one of the salts thereof) with or without other natural polysaccharide(s) and one or more polyols. The formulation is of intra-articular application in the treatment of joint degeneration, in some cases having a rheology similar to that of synovial liquid and always with an elevated resistance to degradation due to a synergistic action between the hyaluronic acid and the polyols.

13 Claims, 6 Drawing Sheets

Figure 1. Frequency scanning, formulation A
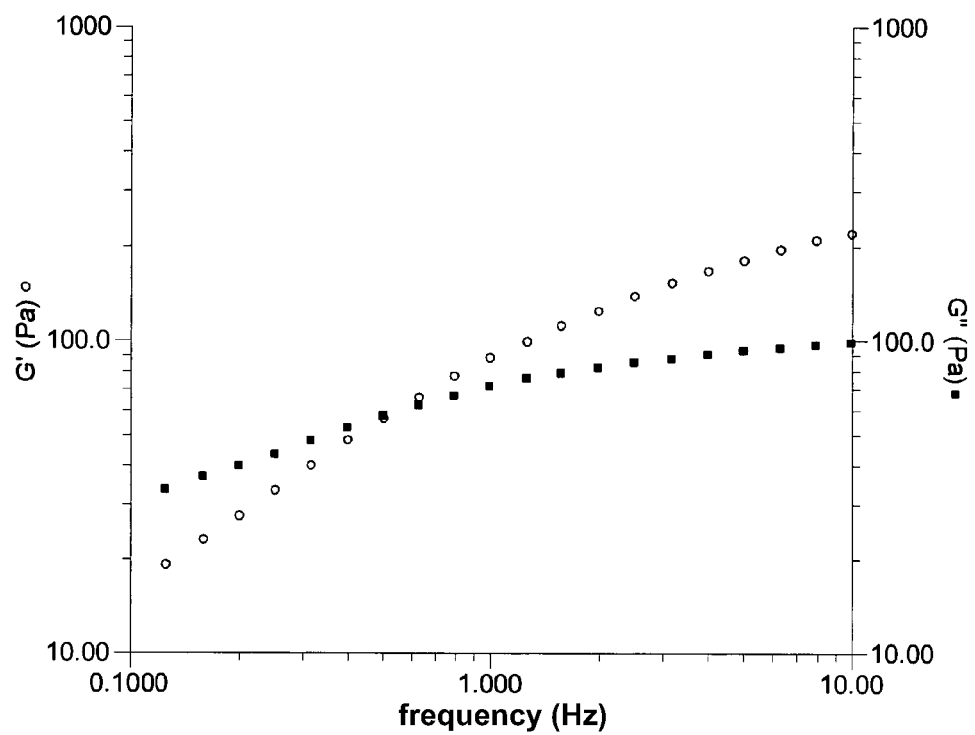
Figure 2. Frequency scanning, formulation B
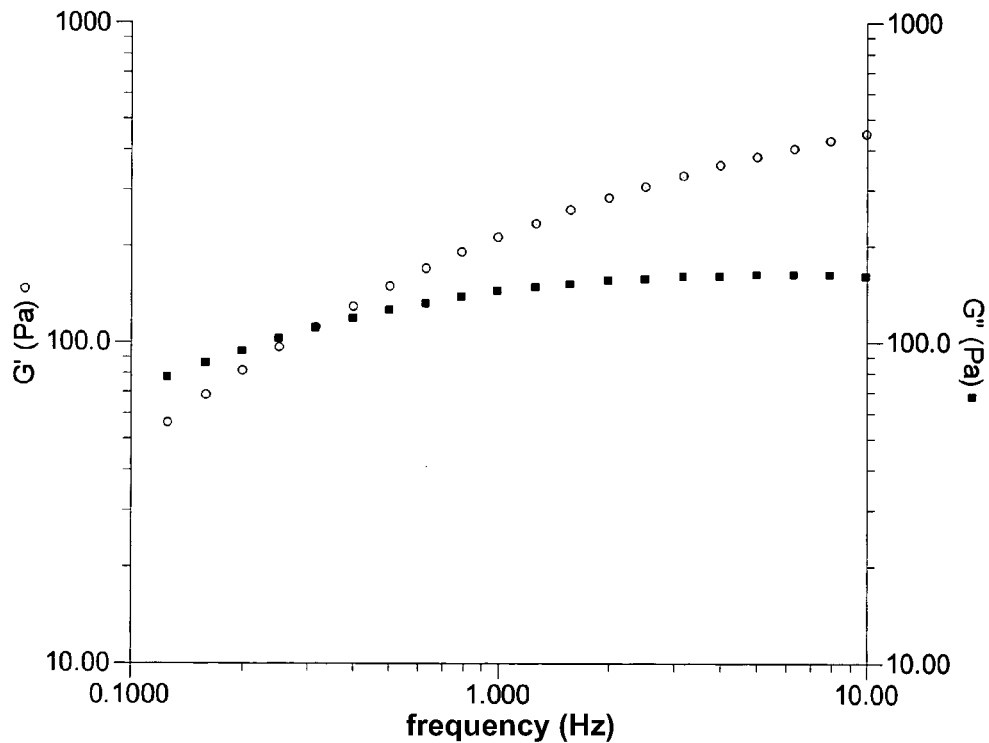

Figure 3. Frequency scanning, formulation C
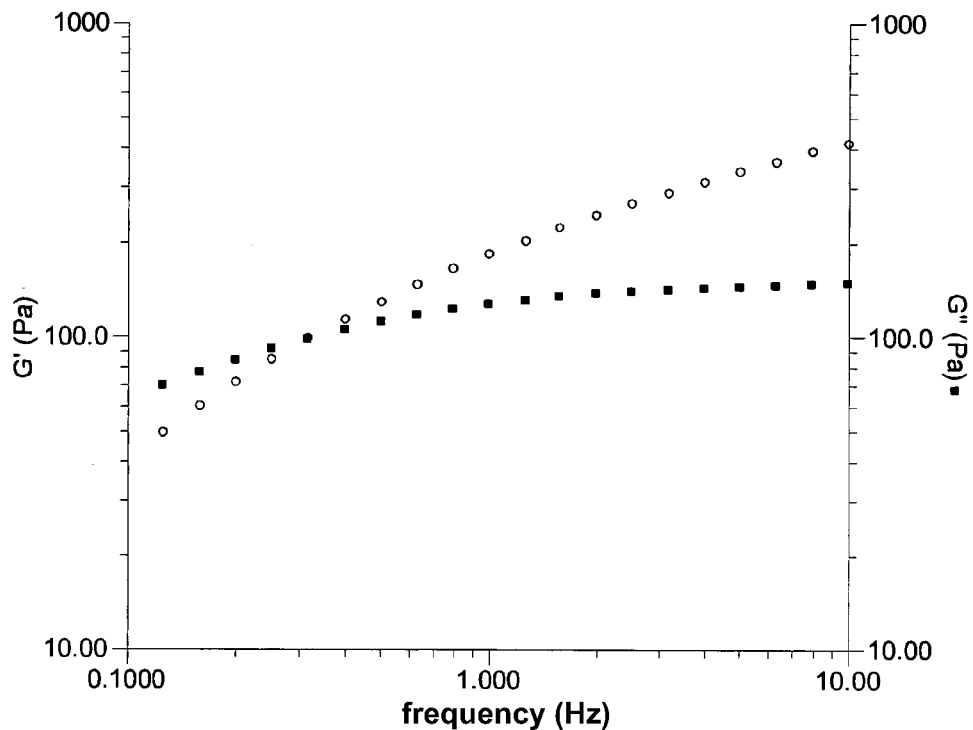
Figure 4. Frequency scanning, formulation D
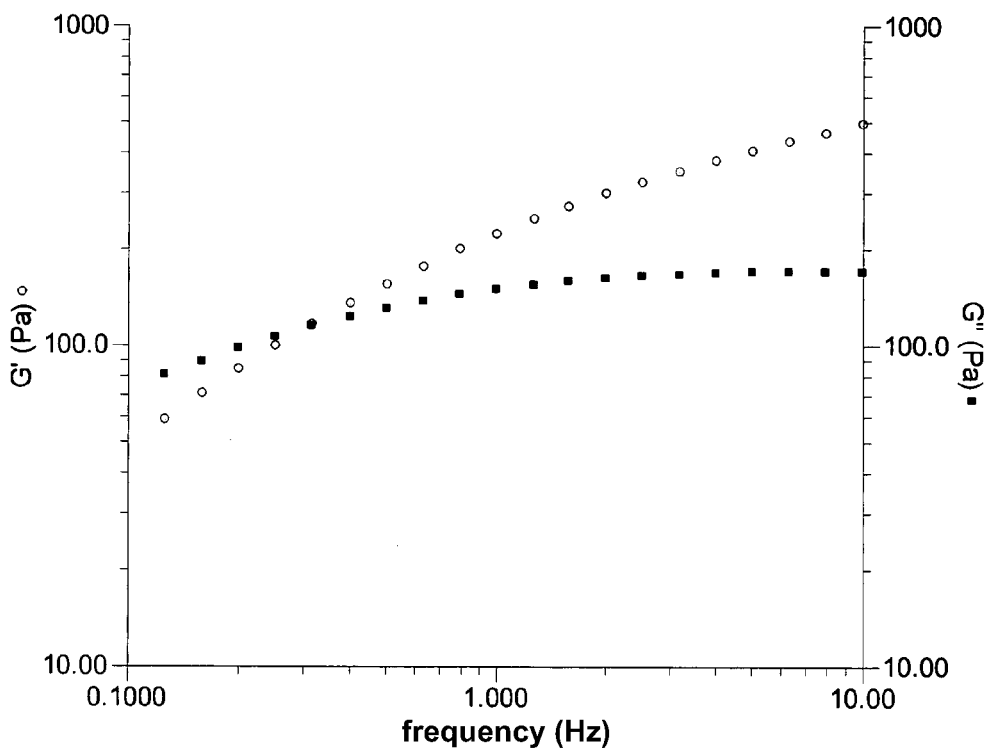

Figure 5. Frequency scanning, formulation E
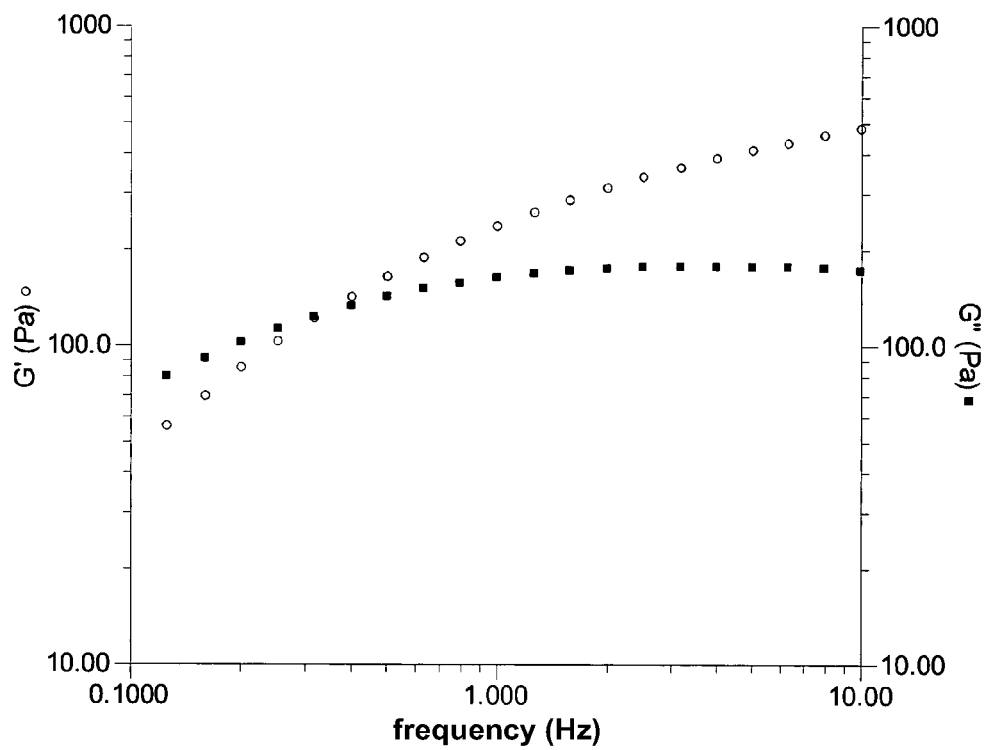
Figure 6. Frequency scanning, formulation P1
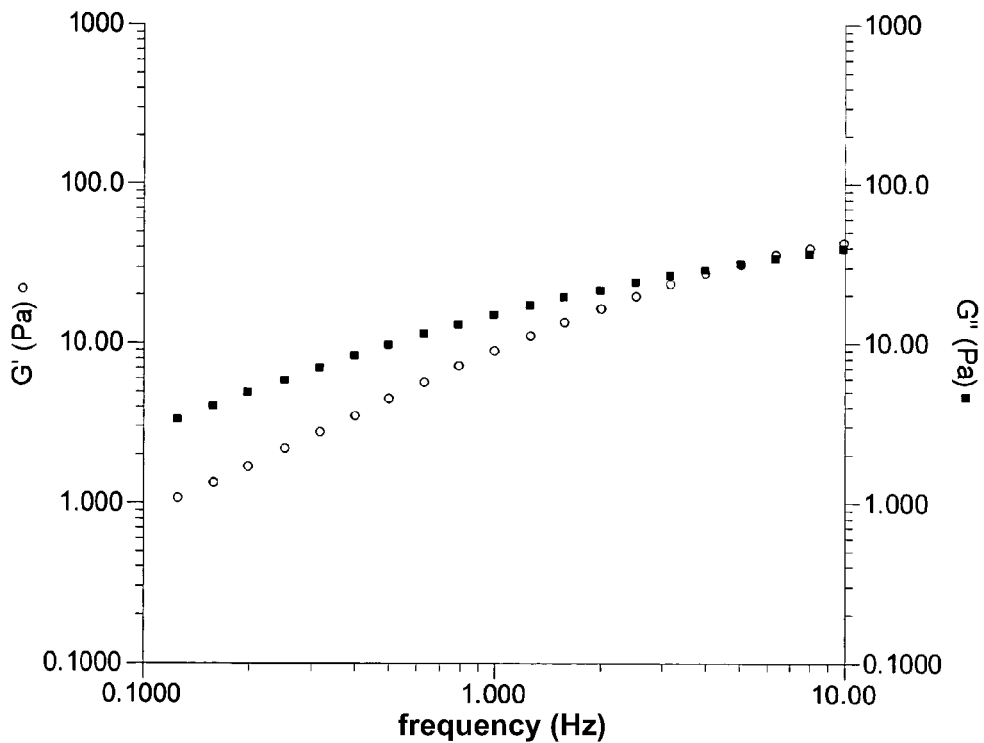

Figure 7. Frequency scanning, formulation P2
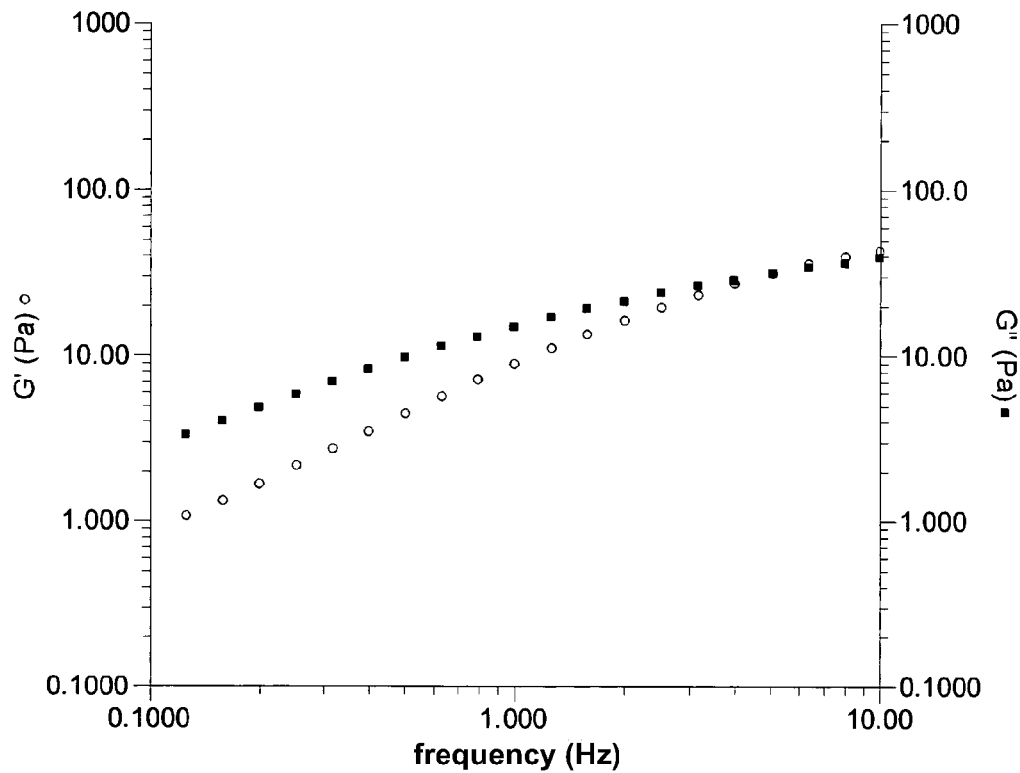
Figure 8. Frequency scanning, formulation P3
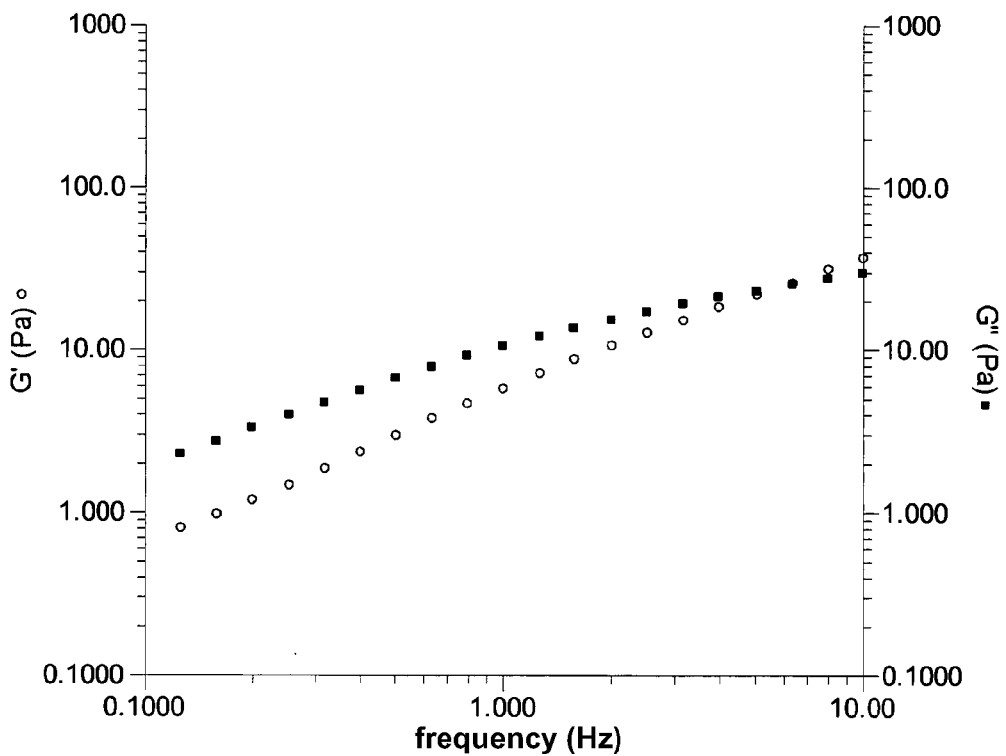

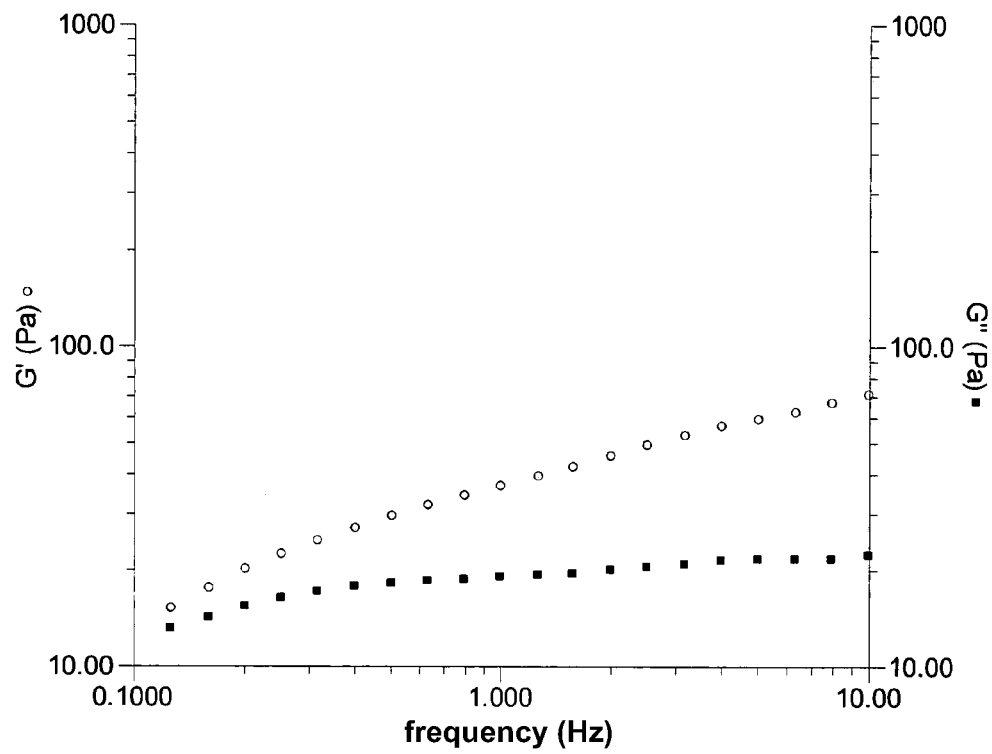
Figure 9. Frequency scanning, formulation P4

Figure 10. *Kinetics of Degradation by the Free Radicals of a Gel According to the Invention and of 3 Commercial Products*
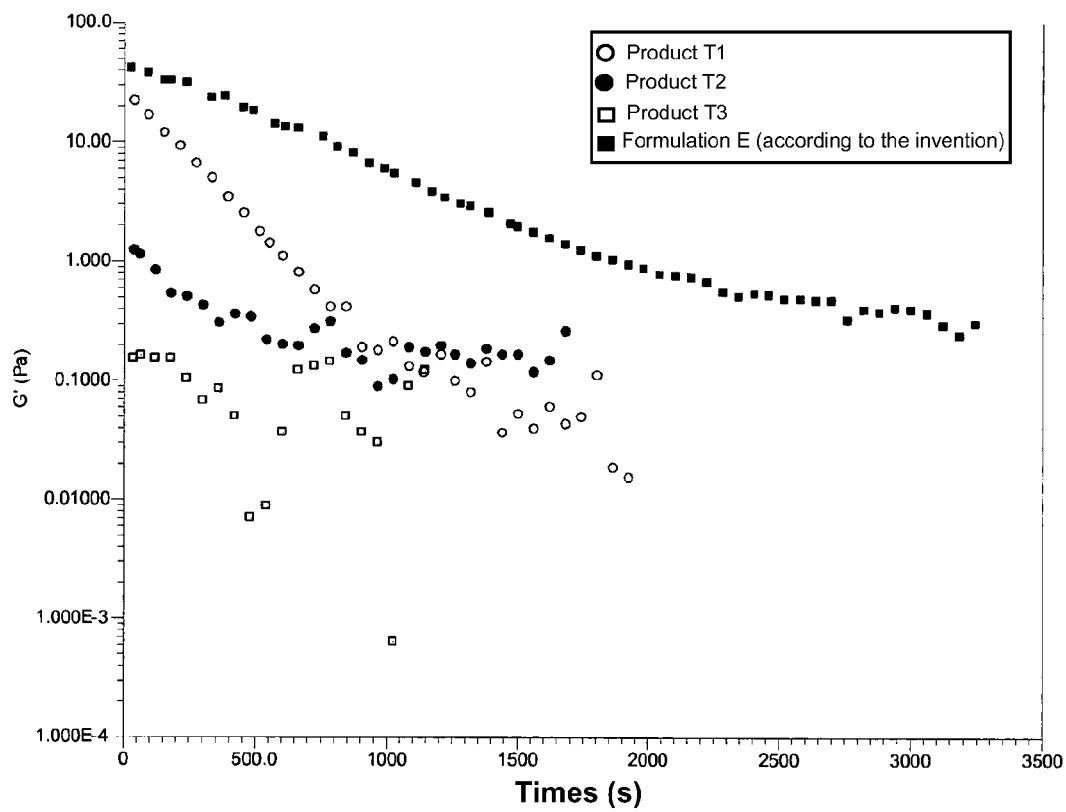
Figure 11. *Demonstration of the Strong Hyaluronic Acid/Polyol Affinity*
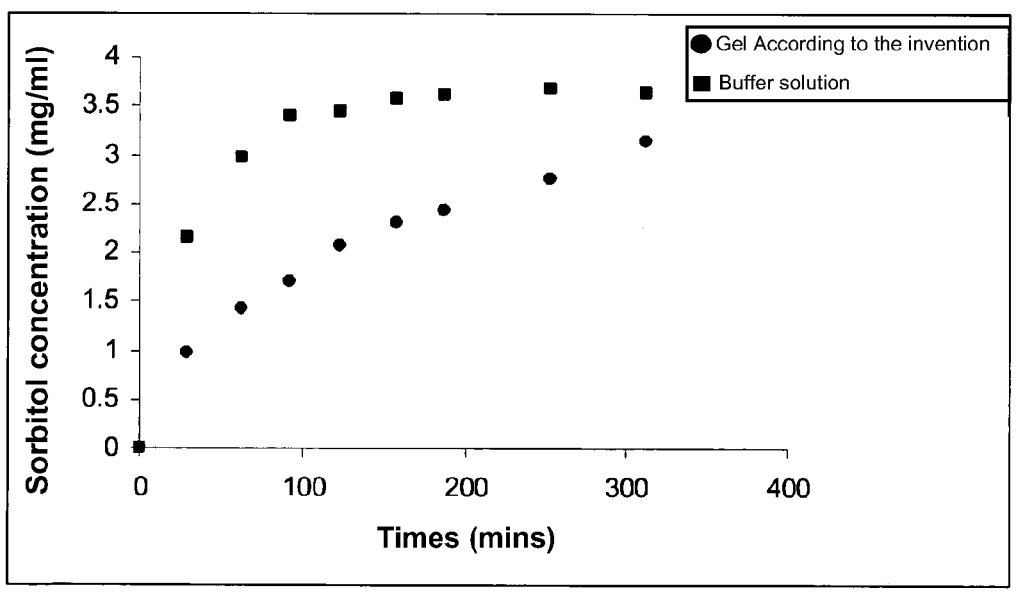

USE OF A NATURAL POLYSACCHARIDE GEL FOR THE PREPARATION OF AN INJECTABLE FORMULATION FOR TREATMENT OF ARTICULAR DEGENERATION

The invention relates to a sterile, injectable aqueous formulation in gel form that consists of hyaluronic acid (or one of its salts) with or without other polysaccharides of natural origin and one or more polyol(s). This injectable formulation is used in intra-articular spaces in the treatment of articular degeneration.

A joint is a junction that makes it possible to connect two bones and to give them mobility relative to one another.

Synovial joints are the most numerous joints, in particular in the limbs. In these joints, the bones are joined via a cavity that is filled with fluid that is both viscous and elastic and that is called synovial fluid.

The sinovial fluid is responsible for the good operation and the protection of joints. It consists in particular of a polysaccharide, hyaluronic acid, which imparts to the synovial fluid viscoelasticity properties that make possible, based on imposed constraints, a lubrication of the joint or an absorption of impacts.

In the case of articular degeneration such as osteoarthritis of the knee (degeneration due in particular to factors such as obesity, heredity, traumas, . . . ), the synovial fluid degrades (reduction of the concentration and the molecular weight of the hyaluronic acid), and this degradation reduces the capacity of the synovial fluid to lubricate the joint and to absorb the impacts.

Treatment by viscosupplementation consists in injecting a gel into the joint so as to replace the deficient synovial fluid. The viscosupplementation can lessen or stop the pain and contribute to restoring the mobility of the joint.

The viscosupplementation products that are currently on the market are gels that contain hyaluronic acid. These gels can be based on hyaluronic acid of animal or non-animal origin and can be cross-linked (the case of Synvisc®, Durolane®) or non-cross-linked (the case of Synocrom®, Arthrum®, Lubravisc®, Structovial®).

It is well known to one skilled in the art that the persistence of a hyaluronic-acid-based gel is low in a joint (from several hours to several days). According to Laurent, "The Chemistry, Biology and Medical Applications of Hyaluronan and its Derivatives, Wenner-Gren International Series, Volume 72," the half-life in a rabbit's joint of a 1% hyaluronan solution is 12 hours, and that of a 0.5% Hylan B gel is 9 days.

This low persistence (kinetics of rapid resorption of gel within the joint) is explained by a degradation (by depolymerization) of the hyaluronic acid. The primary factors of degradation of the hyaluronic acid in the joint are radical degradation, thermal degradation at 37° C., and mechanical degradation (enzymatic degradation is not a significant factor of degradation in the joint). Although the therapeutic effectiveness of the viscosupplement is of longer duration than its dwell time in the joint, the persistence of a gel based on hyaluronic acid in the joint is a prominent parameter that governs the effectiveness of the product. Thus, the longer the dwell time of the hyaluronic-acid-based gel in the joint, the more effective the viscosupplementation treatment (reduction of pain, gain in mobility). Consequently, the increase of dwell time (persistence) of a gel within the joint is a capital point for increasing the effectiveness of a treatment by viscosupplementation using a hyaluronic-acid-based gel.

It is well known by one skilled in the art that the increase in the concentration of hyaluronic acid, the use of high molecular weights of hyaluronic acid and the cross-linking/grafting techniques of the hyaluronic acid make it possible to improve the persistence of a hyaluronic-acid-based gel. However, the optimization of the various parameters listed above does not seem sufficient to allow the persistence of a hyaluronic-acid-based gel to increase significantly in intra-articular spaces (the half-life, within the joint, of current viscosupplementation gels that are on the market is only several days at most).

In a development that was absolutely unexpected and surprising, it was demonstrated that:

The presence of a polyol in a sterile aqueous formulation that is based on hyaluronic acid makes it possible to increase significantly the resistance to the degradation of this gel A strong affinity of the hyaluronic acid and the polyol within the sterile gel involves a slow kinetics for release of the polyol outside of the gel: this affinity between the hyaluronic acid and the polyol involves an effective long-term protection of the gel by the polyol by a synergetic action For a particular composition of an aqueous formulation of hyaluronic acid and a polyol, the sterilization gives this gel viscoelastic properties that are absolutely astonishing in that they virtually reproduce the viscoelastic properties of the uncontaminated synovial fluid—these particular rheological properties of the gel are maintained longer during the period due to the protection against the degradation that is induced by the "hyaluronic acid/polyol" synergy.

This invention therefore consists of a sterile, injectable aqueous formulation in gel form that consists of hyaluronic acid (or one of its salts) with or without other polysaccharides of natural origin and of one or more polyol(s). This formulation, used in the treatment of articular degeneration, in some cases (see Examples 1 and 3) presents a rheology that is close to that of synovial fluid and always an increased resistance to degradation.

Example 4 shows the best resistance of a hyaluronic-acid-based gel and a polyol when the latter is subjected to a radical, thermal and mechanical degradation test. This best resistance of the gel to degradation allows a longer persistence of the gel that is injected into intra-articular spaces.

Example 5 shows the best resistance of a hyaluronic-acid-based gel and a polyol to thermal degradation. This best resistance of the gel to thermal degradation makes possible a longer persistence of the gel that is injected into intra-articular spaces and a better stability of the formulation during storage of the product before use (important point for the expiration period of the product).

Example 8 demonstrates the strong affinity between the hyaluronic acid and a polyol. Injected into the joint, the strong affinity between the hyaluronic acid and the polyol allows a better long-term resistance of the gel to degradation by a synergetic action. Actually, in the case of an injection of a polyol solution into the joint, the natural washing will quickly eliminate the molecule (=polyol) from the joint. In the case of a hyaluronic-acid-based gel with polyol, the strong affinity between the hyaluronic acid and the polyol will prevent the quick release of polyol outside of the gel (and therefore its quick elimination outside of the joint) and will thus make possible effective long-term protection of the gel by polyol against degradation.

Examples 1 and 3 show a rheology of a hyaluronic-acid-based gel and a polyol that is close to that of the synovial fluid.

The publication of MAZZUCCO, D. et al., "Rheology of Joint Fluid in Total Knee Arthroplasty Patients"; *Journal of Orthopedic Research,* 1157-1163, 2002, indicates that the frequency of crossover between the elastic modulus G' and the viscous modulus G" is equal to 0.41±0.12 Hz for an uncontaminated (non-osteoarthritic) synovial fluid of the knee. The value of this crossover frequency is confirmed by the publication of Fam et al., "Rheological Properties of Synovial Fluids," Biorheology, 44, 59-74, 2007. In this publication, a figure has the crossover frequency between the moduli G' and G" of between 0 and 10 Hz for a synovial fluid that belongs to a young or old individual or else for an osteoarthritic synovial fluid.

Below 0.41 Hz: G">G', the synovial fluid has a predominantly viscous function, meaning that the joint is strongly lubricated when the patient is at rest.

Above 0.41 Hz: G'>G", the synovial fluid has a predominantly elastic function, meaning that impacts are strongly absorbed when the patient runs or jumps.

According to one aspect of this invention, the gel that consists of an aqueous solution of hyaluronic acid (or one of its salts) with or without other polysaccharides of natural origin and one or more polyol(s) has, after sterilization, a crossover frequency $f_c$ between the elastic modulus G' and the viscous modulus G" that is close to 0.41 Hz. Thus, the gel has viscoelastic properties that are close to that of the synovial fluid.

As a result, according to one aspect of this invention:

Below $f_c$: G">G', the gel has a predominantly viscous function, meaning that the joint is effectively lubricated when at rest.

Above $f_c$: G'>G", the gel has a predominantly elastic function, meaning that impacts are effectively absorbed when the patient runs or jumps (protection of the joint).

According to one aspect of this invention, the crossover frequency is between 0 and 10 Hz, preferably 0.41±0.41 Hz. This kind of rheology is therefore appropriate to the mechanical constraints of joints and in particular of the knee, the hip or small joints. Consequently, it has a great advantage in the treatment of osteoarthritis by viscosupplementation of the knee or other joints.

FIGS. 1-5 show viscous and elastic moduli of gels according to one aspect of this invention while FIGS. 6-9 show those of commercial gels.

FIGS. 10 and 11 illustrate the kinetics of radical, thermal and mechanical degradation of gels and the hyaluronic acid/polyol affinity.

The invention therefore relates to the use of a sterile, injectable aqueous formulation in gel form that consists of hyaluronic acid (or one of its salts) at 1-100 mg/ml with or without other polysaccharide(s) of natural origin and one or more polyol(s) at 0.0001-100 mg/ml. This injectable formulation in used in intra-articular spaces in the treatment of articular degeneration.

The hyaluronic acid is preferably obtained by biofermentation but it can also be of animal origin. Its molecular weight is 0.1 to $10 \times 10^6$ Da and preferably 2 to $3 \times 10^6$ Da.

The concentration of hyaluronic acid is between 1 and 100 mg/ml and preferably between 10 and 25 mg/ml.

The polysaccharide(s) of natural origin that can be used in combination with the hyaluronic acid is selected from among, for example, chondroitin sulfate, keratan, keratan sulfate, heparin, heparin sulfate, cellulose and its derivatives, chitosan, xanthans, alginates, and all of their respective salts.

Hyaluronic acid, just like the polysaccharide(s) of natural origin, can be cross-linked or non-cross-linked, grafted or non-grafted according to the cross-linking/grafting techniques described in the prior art.

The polyol(s) is/are selected from among, for example, glycerol, propylene glycol, sorbitol, mannitol, erythritol, xylitol, lactitol, maltitol or else cyclic oses such as glucose.

The polyol concentration is between 0.0001 and 100 mg/ml and preferably between 15 and 45 mg/ml.

The aqueous solution that is used is preferably a buffered solution. The composition of this buffer solution is selected so as to have the desired physico-chemical (pH, osmolarity) and rheological properties.

Preferably, the buffer solution that is selected is a phosphate buffer solution.

According to this invention, the formulation is sterilized by the techniques that are well known to one skilled in the art and preferably with the autoclave.

The formulation according to this invention is used by injection into the joint, and the dose that is injected can be between 0.1 and 20 ml based on the nature of the treated joint.

By way of illustration, two viscoelastic gel formulations that can be prepared according to this invention are provided below:

Viscoelastic gel based on hyaluronic acid and glycerol
Sterile solution that consists of 20 mg/ml of hyaluronic acid (MM=$2.5 \times 10^6$ D) and 20 mg/ml of glycerol in the phosphate buffer.

Viscoelastic gel based on hyaluronic acid and sorbitol
Sterile solution that consists of 20 mg/ml of hyaluronic acid (MM=$2.5 \times 10^6$ D) and 40 mg/ml of sorbitol in the phosphate buffer.

EXAMPLES

Examples are proposed so as to illustrate the invention but are in no way limiting of said invention. The formulations that are prepared in the following examples are gels based on sodium hyaluronate (NaHA) that are non-cross-linked or cross-linked with polyol.

The preparation of non-cross-linked or cross-linked gels is carried out according to the techniques that are well known by one skilled in the art. The sodium hyaluronate that is used to produce these gels has a molecular weight that is equal to $2.5 \times 10^6$ Da. In the case of the cross-linked gels, the cross-linking agent that is used is BDDE, and the definition of the cross-linking level that is used is: weight (BDDE)/weight (dry NaHA).

The incorporation of polyol in the gel is carried out by adding the necessary amount of polyol in the non-cross-linked or cross-linked gel and by mixing it with the spatula for 10 minutes (per 100 g of final gel).

The prepared gels are filled into glass syringes and then sterilized with moist heat (T=121° C.).

The rheometer that is used to carry out the rheological measurements is an AR1000 (TA Instruments) with a flat geometry of 40 mm, a gap of 1000 microns, and an analytical temperature of 37° C.

The metering of the polyols is carried out by an HPLC Ultimate 3000 (Dionex) and an ion exchange column.

Example 1

Preparation of Sterile Injectable Formulations According to the Invention

Formulation A: Gel based on non-cross-linked NaHA with glycerol
15 mg of NaHA at $2.5 \times 10^6$ D
20 mg of glycerol
Enough for 1 ml of phosphate buffer Formulation B: Gel based on non-cross-linked NaHA with glycerol
  15 mg of NaHA at $2.5 \times 10^6$ D
  20 mg of glycerol
  Enough for 1 ml of phosphate buffer
Formulation C: Gel based on non-cross-linked NaHA with propylene glycol
  20 mg of NaHA at $2.5 \times 10^6$ D
  20 mg of propylene glycol
  Enough for 1 ml of phosphate buffer
Formulation D: Gel based on non-cross-linked NaHA with mannitol
  20 mg of NaHA at $2.5 \times 10^6$ D
  15 mg of mannitol
  Enough for 1 ml of phosphate buffer
Formulation E: Gel based on non-cross-linked NaHA with sorbitol
  20 mg of NaHA at $2.5 \times 10^6$ D
  40 mg of sorbitol
  Enough for 1 ml of phosphate buffer
Formulation F: Gel based on cross-linked NaHA with sorbitol
  18 mg of NaHA at $2.5 \times 10^6$ D, cross-linking level=6%
  50 mg of sorbitol
  Enough for 1 ml of phosphate buffer Example 2

Physicochemical Properties of the Formulations of Example 1 pH (at ambient temperature)

| Formulation | pH |
|---|---|
| A | 7.0 |
| B | 7.2 |
| C | 7.1 |
| D | 7.0 |
| E | 7.1 |
| F | 7.1 |

Osmolarity

| Formulation | Osmolarity (mOsm/kg) |
|---|---|
| A | 335 |
| B | 322 |
| C | 324 |
| D | 315 |
| E | 326 |
| F | 338 |

The formulations A, B, C, D, E and F are isotonic and have a neutral pH.

Example 3

Rheological Properties of the Formulations of Example 1

The viscoelastic properties of the formulations A, B, C, D and E are characterized by measuring the evolution of the viscous modulus (G") and the elastic modulus (G') based on frequency (see FIGS. 1 to 5).

For these 5 formulations, it is noted that the crossover frequency of the modulus G' and the modulus G" is close to that of the uncontaminated synovial fluid.

The table below provides crossover frequency values $f_c$ for each formulation and for uncontaminated synovial fluid.

| Formulation | Crossover Frequency $f_c$ (Hz) |
|---|---|
| A | 0.50 |
| B | 0.32 |
| C | 0.32 |
| D | 0.32 |
| E | 0.33 |
| Uncontaminated Synovial Fluid (Publication by Mazzucco, D. et al.) | $0.41 \pm 0.12$ |

As described in this invention:
Below $f_c$: G">G', the gel has a predominantly viscous function, meaning that the joint is effectively lubricated when at rest.
Above $f_c$: G'>G", the gel has a predominantly elastic function, meaning that impacts are effectively absorbed when the patient runs or jumps Example 4

Resistance to Degradation of the Formulations of Example 1

To show that the presence of a polyol in an NaHA-based gel makes it possible to reduce the degradation of the gel by a radical, thermal and mechanical action, the resistance to the degradation of NaHA-based gels with polyol (formulations of Example 1) and the resistance to the degradation of NaHA-based gels without polyol (=reference gels) were compared.

For the formulations B, C, D and E of Example 1, the NaHA-based reference gel without polyol is a non-cross-linked NaHA-based gel with 20 mg/ml of NaHA (MM=$2.5 \times 10^6$ D, in the phosphate buffer)—formulation G.

For the formulation F of Example 1, the NaHA-based reference gel without polyol is a cross-linked NaHA-based gel with 18 mg/ml of NaHA (MM=$2.5 \times 10^6$ D before cross-linking, in the phosphate buffer) that has a cross-linking level of 6%—formulation H.

The degradation test is carried out by adding an oxidizing agent to the gel to be tested, by homogenizing the mixture with the spatula for 1 minute, by being brought to the temperature of 37° C., and by imposing a deformation of 0.3%. The value of the parameter $\tan \delta = G''/G'$ at 0.7 Hz (characteristic parameter of the viscoelastic properties of the gel) is measured over time.

It is noted that this parameter increases over time, synonymous with a gradual breakdown of the gel. The values that are measured at t=0 and t=15 minutes for the formulations B, C, D, E, F, G and H are provided in the table below.

| Formulation | Tanδ (t = 0 min) | Tanδ (t = 15 min) | ΔTanδ (%) |
|---|---|---|---|
| B | 1.10 | 3.34 | +204% |
| C | 1.08 | 3.13 | +205% |
| D | 1.19 | 4.63 | +289% |
| E | 1.08 | 2.57 | +138% |
| F | 0.74 | 0.80 | +8% |
| G | 1.41 | 6.56 | +365% |
| H | 0.74 | 0.93 | +26% |

As described in this invention, each formulation B, C, D and E has a resistance to degradation that is significantly higher than that of the gel without polyol (formulations G). Likewise, the formulation F has a resistance to degradation that is significantly higher than that of the corresponding gel without polyol (formulations H).

Consequently, the polyols protect the gel effectively against degradation.

Example 5

Study of Accelerated Aging of a Formulation with and without Polyol

Two formulations are subjected to accelerated furnace aging at 40° C.:
Formulation B of Example 1: Solution based on hyaluronic acid and glycerol
Formulation G without addition of alcohol (described in Example 4)
20 mg of hyaluronic acid with $2.5 \times 10^6$ D
Enough for 1 ml of phosphate buffer A measurement of zero viscosity (zero-shear viscosity) and a determination of the crossover frequency $f_c$ between the elastic modulus G' and the viscous modulus G" is carried out at 3 times (t=0, 7 days, 26 days)

The results that are obtained are provided in the table below:

| Number of Days of Aging at 40° C. | Formulation | Zero Viscosity | Zero Viscosity Variation Relative to to (%) | $f_c$ (Hz) | Variation of $f_c$ Relative to to (%) |
|---|---|---|---|---|---|
| 0 Day | B | 252 | / | 0.32 | / |
|  | G | 192 | / | 0.39 | / |
| 7 Days | B | *ND | / | 0.32 | 0% |
|  | G | *ND | / | 0.39 | 0% |
| 26 Days | B | 210 | −17% | 0.37 | +16% |
|  | G | 143 | −26% | 0.50 | +28% |

*ND = Not Determined

It is noted that during the accelerated aging, the loss of zero viscosity and the offsetting of the crossover frequency $f_c$ are less in the case of the formulation B (formulation according to this invention) than in the case of the formulation without polyol (formulation G).

Example 6

Comparison of the Rheology of 4 Commercial Viscosupplementation Products and a Formulation that is Obtained According to this Invention The tested products are as follows:

| Product | Trade Name | Manufacturer | Concentration of Hyaluronic Acid (mg/ml) | Molecular Weight of Hyaluronic Acid (Da) | Sterilization Method |
|---|---|---|---|---|---|
| P1 | Synocrom ® | CROMA PHARMA | 10 | $2.2\text{-}2.7 \cdot 10^6$ | Moist Heat |
| P2 | Structovial ® | CROMA PHARMA | 10 | $2.2\text{-}2.7 \cdot 10^6$ | Moist Heat |
| P3 | Fermathron ® | HYALTECH | 10 | $1 \cdot 10^6$ | Filtration |
| P4 | Lubravisc ® | BOHUS BIOTECH | 10 | $4 \cdot 10^6$ | Moist Heat |
| Formulation A of Example 1 | Not Applicable | Not Applicable | 15 (+20 mg/ml of Glycerol) | $2.5 \cdot 10^6$ | Moist Heat |

For the 5 gels tested, FIGS. 6-9 provide the viscous modulus (G") and the elastic modulus (G') based on the frequency.

It is noted that only the gel according to Example 1 has a crossover frequency (0.50 Hz) that is close to that of the uncontaminated synovial fluid (0.41 Hz).

The table below combines the values of the crossover frequencies $f_c$ for the products P1 to P4 and for the formulation A of Example 1.

| Product | $f_c$ (Hz) |
|---|---|
| Formulation A of Example 1 | 0.50 |
| P1 | 5.8 |
| P2 | 5.0 |
| P3 | 6.3 |
| P4 | 0.09 |

It is known that according to the publication of Mazzucco, D. et al. (cited above), the crossover frequency of the uncontaminated synovial fluid (0.41 Hz) is below the frequencies that are observed in the knee during walking (0.7 Hz) and running (3 Hz).

For the products P1 to P3, the crossover frequency is higher than 3 Hz, and, consequently, the products do not have strong elasticity allowing the absorption of impacts when the knee is moving.

The product P4 has a very low crossover frequency; the elastic modulus is higher than the viscous modulus over the entire frequency range of 0.1-10 Hz. Consequently, the elasticity is high when the knee is moving, but the lubrication of the joint is not very effective when the patient is at rest.

Example 7

Comparison of the Resistance to Degradation of 3 Commercial Viscosupplementation Products and a Formulation that is Obtained According to this Invention The tested products are as follows:

| Product | Trade Name | Manufacturer | Concentration of Hyaluronic Acid (mg/ml) |
|---|---|---|---|
| T1 | Arthrum ® | LCA Pharmaceutical | 20 |
| T2 | Ostenil ® | TRB Chemedica | 10 |
| T3 | Synocrom ® | CROMA PHARMA | 10 |
| Formulation E of Example 1 | Not Applicable | Not Applicable | 20 (+40 mg/ml of Sorbitol) |

The degradation test is carried out according to the method that is described in Example 4.

The value of the parameter G' at 0.7 Hz is tracked over time.

The thus obtained rheology curves are provided in FIG. 10.

It is noted that the gel according to this invention becomes significantly degraded less quickly than the 3 commercial products tested.

Example 8

Demonstration of the Strong Hyaluronic Acid/Polyol Affinity

So as to demonstrate the strong affinity between the hyaluronic acid and the polyol and therefore the long-term protection of the gel by the polyol, a follow-up study of the release of a polyol by dialysis has been carried out.

5 g of the formulation E (gel based on 20 mg/ml of non-cross-linked NaHA and 40 mg/ml of sorbitol—Example 1) was introduced into a dialysis membrane (No. 1) (Spectra/Pore®, MWCO: 12-14,000).

5 g of a phosphate buffer solution that contains 40 mg/ml of sorbitol was introduced into a $2^{nd}$ dialysis membrane (No. 2) (Spectra/Pore®, MWCO: 12-14,000)—same dimension as the membrane No. 1.

These membranes were placed in respective bottles containing 50 g of purified water (=dialysis bath) while being stirred magnetically. Measurements of sorbitol concentration by HPLC were carried out in the dialysis baths at different times so as to track the kinetics for release of sorbitol outside of the membrane with gel or a buffer solution.

The tracking curves of the sorbitol concentration over time are provided in FIG. 11.

The kinetics for release of sorbitol into a gel is significantly slower than in a buffer solution.

This study promotes the synergy between the hyaluronic acid and the polyol that is present in the gel: the strong hyaluronic acid/polyol affinity makes it possible for the polyol to be present within the gel over a long period, and the protection capacity of the polyol with regard to the gel makes it possible to have a strong long-term resistance of the gel against degradation.

The invention claimed is:

1. A sterile, injectable and viscoelastic aqueous gel for injection into intra-articular spaces of a subject, comprising:
   hyaluronic acid or a salt thereof at a concentration of 10-25 mg/ml, the hyaluronic acid being non-cross-linked and having a molecular weight of $2 \times 10^6$ to $3 \times 10^6$ Da;
   one or more polyols selected from the group consisting of propylene glycol, sorbitol, mannitol, and mixtures thereof, at a concentration of 10-45 mg/ml; and
   a physiologically acceptable buffer,
   wherein,
   the gel has been moist heat sterilized,
   the gel is injectable into the intra-articular space of a subject, and
   the gel has a crossover frequency point between an elastic modulus G' and a viscous modulus G" in a range of greater than zero to 0.82 Hz, and G' is greater than G" at the frequencies higher than the crossover frequency point.

2. The gel according to claim 1, comprising hyaluronic acid at a concentration of 20 mg/ml.

3. The gel according to claim 1, wherein the concentration of the one or more polyols is 15 to 45 mg/ml.

4. The gel according to claim 1, comprising hyaluronic acid at a concentration of 20 mg/ml and sorbitol at a concentration of 40 mg/ml.

5. The gel according to claim 1, wherein the polyol is one of sorbitol, mannitol or a mixture thereof.

6. The gel according to claim 1, wherein the moist heat sterilizing is carried out in an autoclave.

7. The gel according to claim 1, wherein the gel has a cross-over frequency point in a range of 0.32 to 0.50 Hz.

8. The gel according to claim 1, wherein the gel has a crossover frequency point in a range of 0.41±0.12 Hz.

9. The gel according to claim 1, further comprising one or more other polysaccharides of natural origin, other than hyaluronic acid.

10. A process for preparing the sterile, injectable aqueous gel according to claim 1, comprising:
    preparing an aqueous composition comprising the hyaluronic acid or salt thereof and the one or more polyols, and
    moist heat sterilizing the composition to obtain the gel.

11. The process according to claim 10, wherein the moist heat sterilizing is carried out in an autoclave.

12. The gel according to claim 9, wherein the one or more other polysaccharides of natural origin is selected from the group consisting of: chondroitin sulfate, keratan, keratan sulfate, heparin, heparin sulfate, cellulose and its derivatives, chitosan, xanthans, alginates, and respective salts thereof.

13. A process for preparing the gel according to claim 9, comprising:
    preparing an aqueous composition comprising the hyaluronic acid or salt thereof, the one or more other polysaccharides of natural origin, and the one or more polyols, and
    moist heat sterilizing the composition to obtain the gel.

* * * * *